United States Patent
Hindley et al.

[11] Patent Number: 5,478,850
[45] Date of Patent: Dec. 26, 1995

[54] THIAZOLIDINEDIONE DERIVATIVES

[75] Inventors: Richard M. Hindley; David Haigh; Graham P. Cottam, all of Epsom, England

[73] Assignee: Beecham Group plc, Great Britain

[21] Appl. No.: 50,116

[22] PCT Filed: Oct. 18, 1991

[86] PCT No.: PCT/GB91/01835

§ 371 Date: Apr. 30, 1993

§ 102(e) Date: Apr. 30, 1993

[87] PCT Pub. No.: WO92/07839

PCT Pub. Date: May 14, 1992

[30] Foreign Application Priority Data

Oct. 30, 1990 [GB] United Kingdom ............... 9023585

[51] Int. Cl.$^6$ ............... C07D 277/34; A61K 31/425
[52] U.S. Cl. ............... 514/369; 548/181; 548/183
[58] Field of Search ............... 548/183, 181; 514/369

[56] References Cited

U.S. PATENT DOCUMENTS 5,260,445  11/1993  Hindley ............... 548/183

FOREIGN PATENT DOCUMENTS 0008203  2/1980  European Pat. Off. .
0295828  12/1988  European Pat. Off. .
0332332  9/1989  European Pat. Off. .

Primary Examiner—Robert Gerstl
Attorney, Agent, or Firm—Charles M. Kinzig; Stephen Venetianer; Edward T. Lentz

[57] ABSTRACT

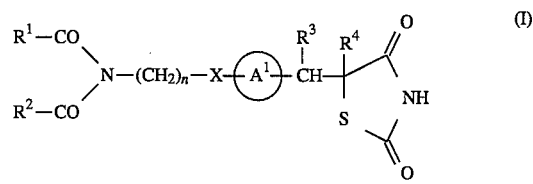

A compound of formula (I) or a tautomeric form thereof and/or a pharmaceutically acceptable salt thereof, and/or a pharmaceutically acceptable solvate thereof, wherein $R^1$ and $R^2$ each independently represent an alkyl group, a substituted or unsubstituted aryl group or an aralkyl group being substituted or unsubstituted in the aryl or alkyl moiety; or $R^1$ together with $R^2$ represents a linking group, the linking group consisting of an optionally substituted methylene group and either a further optionally substituted methylene group or an O or S atom, optional substituents for the said methylene groups being selected from alkyl, aryl or aralkyl or substituents of adjacent methylene groups together with the carbon atoms to which they are attached form a substituted or unsubstituted phenylene group; $R^3$ and $R^4$ each represent hydrogen, or $R^3$ and $R^4$ together represent a bond; $A^1$ represents a benzene ting having in total up to three optional substituents; X represents O or S; and n represents an integer in the range of from 2 to 6; a process for preparing such a compound, a pharmaceutical composition containing such a compound and the use of such a compound and composition in medicine.

15 Claims, No Drawings

THIAZOLIDINEDIONE DERIVATIVES

This invention relates to certain novel compounds, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581 and 0208420 relate to thiazolidinedione derivatives which are disclosed as having hypoglycaemic and hypolipidaemic activity. Chem. Pharm. Bull 30 (10) 3580–3600 also relates to certain thiazolidinedione derivatives having hypoglycaemic and hypolipidaemic activities.

It has now surprisingly been discovered that certain novel imide-substituted thiazolidinedione derivatives show improved blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

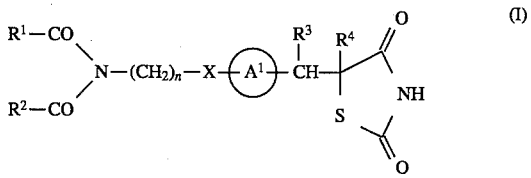

or a tautomeric form thereof and/or a pharmaceutically acceptable salt thereof, and/or a pharmaceutically acceptable solvate thereof, wherein:

$R^1$ and $R^2$ each independently represent an alkyl group, a substituted or unsubstituted aryl group or an aralkyl group being substituted or unsubstituted in the aryl or alkyl moiety;

or $R^1$ together with $R^2$ represents a linking group, the linking group consisting of an optionally substituted methylene group and either a further optionally substituted methylene group or an O or S atom, optional substituents for the said methylene groups being selected from alkyl, aryl or aralkyl or substituents of adjacent methylene groups together with the carbon atoms to which they are attached form a substituted or unsubstituted phenylene group;

$R^3$ and $R^4$ each represent hydrogen, or $R^3$ and $R^4$ together represent a bond;

$A^1$ represents a benzene ring having in total up to three optional substituents;

X represents O or S; and n represents an integer in the range of from 2 to 6.

When $R^1$ or $R^2$ represents an aryl group, the aryl group is suitably an unsubstituted aryl group.

When $R^1$ or $R^2$ represents an aralkyl group, the aralkyl group is suitably of formula aryl($CH_2$)m, wherein m is 1, 2, 3 or 4, preferably 1 or 2; preferably the aryl moiety is unsubstituted.

Suitably $R^1$ together with $R^2$ represents a linking group, the linking group consisting of an optionally substituted methylene group and either a further optionally substituted methylene group or an O or S atom, optional substituents for the said methylene groups being selected from alkyl, aryl or aralkyl or substituents of adjacent methylene groups together with the carbon atoms to which they are attached form a substituted or unsubstituted phenylene group;

Favourably, the linking group consists of an optionally substituted methylene group and an O or S atom, preferably an S atom; preferred substituents are aryl, for example phenyl, or aralkyl, for example benzyl, groups.

Favourably, the linking group consists of two optionally substituted methylene groups.

When the linking group consists of two optionally substituted methylene groups it is preferred if the substituents of the adjacent methylene groups together with the carbon atoms to which they are attached form a substituted, or suitably, unsubstituted phenylene group.

Favoured optional substituents for the methylene groups forming the linking group include $C_{1-6}$-alkyl, phenyl and benzyl groups.

Optional substituents for the phenylene group, forming part of the linking group, are selected from halogen, alkyl, phenyl, alkoxy, haloalkyl, hydroxyalkyl, hydroxy, amino, nitro, cyano, carboxy, alkoxycarbonyl, alkoxycarbonylalkyl, alkylcarbonyloxy and alkylcarbonyl groups.

Suitably, $R^3$ and $R^4$ each represent hydrogen.

Suitable substituents for the moiety $A^1$ include halogen, substituted or unsubstituted alkyl or alkoxy.

Favourably, $A^1$ represents a moiety of formula (a):

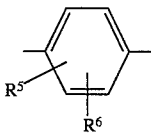

wherein $R^5$ and $R^6$ each independently represent hydrogen, halogen, substituted or unsubstituted alkyl or alkoxy.

Suitably, $R^5$ and $R^6$ each independently represent hydrogen, halogen, alkyl or alkoxy.

Preferably, $R^5$ and $R^6$ each represent hydrogen.

In one aspect, X represents sulphur.

Preferably, X represents oxygen.

Suitably, n represents an integer 2, 3 or 4, notably 2 or 3 and especially 2.

As indicated above a compound of formula (I) may exist in one of several tautomeric forms, all of which are encompassed by the present invention. It will be appreciated that the present invention encompasses all of the isomeric forms of the compounds of formula (I) and the pharmaceutically acceptable salts thereof, including any stereoisomeric forms thereof, whether as individual isomers or as mixtures of isomers.

When used herein the term 'aryl' or the term 'ar' (as used for example in 'aralkyl') includes phenyl and naphthyl optionally substituted with up to five, preferably up to three, groups selected from halogen, alkyl, phenyl, alkoxy, haloalkyl, hydroxyalkyl, hydroxy, amino, nitro, cyano, carboxy, alkoxycarbonyl, alkoxycarbonylalkyl, alkylcarbonyloxy, or alkylcarbonyl groups.

A preferred aralkyl group is a benzyl group.

When used herein the term 'halogen' refers to fluorine, chlorine, bromine and iodine; preferably chlorine.

When used herein the term 'alkyl' (when used alone or as part of another group such as aralkyl) or 'alk' (as used for example in 'alkoxy') relate to alkyl groups having straight or branched carbon chains, containing up to 12 carbon atoms.

Suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups.

Suitable substituents for any alkyl group include those mentioned hereinbefor in relation to aryl groups.

Suitable pharmaceutically acceptable salts include salts of the thiazolidinedione moiety, and, where appropriate, salts of carboxy groups.

Suitable pharmaceutically acceptable salts of the thiazolidinedione moiety include metal salts especially alkali metal salts such as the lithium, sodium and potassium salts.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable solvates include hydrates.

In a further aspect the present invention also provides a process for the preparation of a compound of formula (I), or a tautomeric form thereof, and/or a pharmaceutically acceptable salt thereof, and/or a pharmaceutically acceptable hydrate thereof, which process comprises reacting a compound of formula (II):

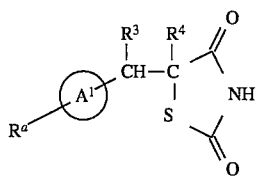
(II)

wherein $R^3$ $R^4$ and $A^1$ are as defined in relation to formula (I), and $R^a$ is a moiety convertible to a moiety of formula (b):

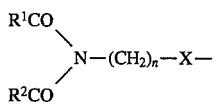
(b)

wherein $R^1$, $R^2$, X and n are as defined in relation to formula (I), with an appropriate reagent capable of converting $R^a$ to the said moiety (b) and thereafter, if required, carrying out one or more of the following optional steps:

(i) converting a compound of formula (I) into a further compound of formula (I);

(ii) preparing a pharmaceutically acceptable salt of the compound of formula (I) and/or a pharmaceutically acceptable solvate thereof.

Suitably, $R^a$ represents —XH, wherein X is defined relation to formula (I).

Alternatively $R^a$ represents a leaving group or atom, such as a halogen atom, preferably a fluorine atom.

When $R^a$ is —XH, an appropiate reagent is a compound of formula (III):

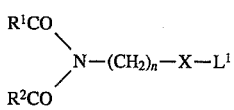
(III)

wherein $R^1$ $R^2$ X and n are as defined in relation to formula (I) and $L^1$ represents a leaving group such as a mesyl or tosyl group.

The reaction between the compounds of formulae (II) and (III) may be carried out in any suitable aprotic solvent, for example dimethylformamide, at any temperature providing a suitable rate of formation of the required product, conveniently at an elevated temperature, for example in the range of from 60° C to 100° C; preferably the reaction is carried out in the presence of a base, such as sodium hydride, in an inert atmosphere.

When $R^a$ is a leaving group or atom such as a halogen atom preferably a fluorine atom, a suitable reagent is a compound of formula (V) as defined hereinafter.

A compound of formula (II) may be prepared by reacting a compound of formula (IV):

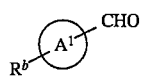
(IV)

wherein $A^1$ is as defined in relation to formula (I), and $R^b$ represents $R^a$ or a protected form thereof, with 2,4-thiazolidinedione or a protected form thereof; and thereafter, if required, reducing a compound of formula (II) wherein $R^3$ and $R^4$ together represent a bond to give a compound of formula (II) wherein $R^3$ and $R^4$ each represent hydrogen and/or removing any protecting group.

The reaction between the compound of formula (IV) and 2,4-thiazolidinedione will of course be carried out under conditions suitable to the nature of the compound of formula (IV), in general the reaction being carried out in a solvent such as toluene, suitably at an elevated temperature such as the reflux temperature of the solvent and preferably in the presence of a suitable catalyst such as piperidinium acetate or benzoate. Favourably, in the reaction between the compound of formula (IV) and 2,4-thiazolidinedione, the water produced in the reaction is removed from the reaction mixture, for example by means of a Dean and Stark apparatus.

For compounds of formula (II) wherein $R^a$ is HX—, $R^b$ is preferably a protected form of HX—, for example $R^cX$— wherein $R^c$ is a benzyl group.

A compound of formula (III) wherein $L^1$ is a leaving group may be prepared by suitable conversion of a compound of formula (IV):

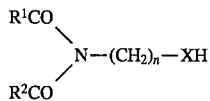
(V)

wherein $R^1$ $R^2$ X and n are as defined in relation to formula (I), for example when $L^1$ in (III) represents mesyl or tosyl, by mesylation or tosylation in an inert solvent such as dichloromethane at any temperature providing a suitable rate of formation of the required product, conveniently at room temperature or lower, for example at 0° C., and preferably in the presence of a base such as triethylamine.

A compound of formula (V) may be prepared by reacting a compound of formula (VI):

(VI)

wherein $R^1$ and $R^2$ are as defined in relation to formula (I), with a compound of formula (VII):

$L^2$—$(CH_2)_n XR^c$ (VII)

wherein X and n are as defined in relation to formula (I), $L^2$ represents a leaving group such as a chlorine atom and $R^c$ represents hydrogen or a protecting group.

The reaction between the compounds of formulae (VI) and (VII) may be carried out using any suitable aprotic solvent such as dimethylformamide in the presence of a base such as sodium hydride or sodium carbonate, at a temperature providing a convenient rate of formation of the required product, suitably at room temperature.

The compounds of formula (VI) and (VII) are either known compounds or are prepared using methods analogous to those used to prepare known compounds.

Preferably, X represents O.

A compound of formula (I), or a tautomeric form thereof, and/or a pharmaceutically acceptable salt thereof and/or a pharmaceutically acceptable solvate thereof, may also be prepared by reacting a compound of formula (VIII):

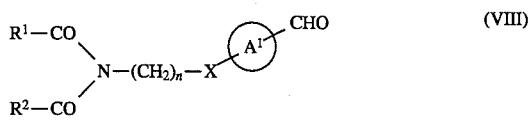

wherein $R^1$, $R^2$, $A^1$, X and n are as defined in relation to formula (I) with 2,4-thiazolidinedione; and thereafter if required carrying out one or more of the following optional steps:

(i) converting a compound of formula (I) into a further compound of formula (I);

(ii) preparing a pharmaceutically acceptable salt of a compound of formula (I) and/or a pharmaceutically acceptable solvate thereof.

The reaction between a compound of formula (VIII) and 2,4-thiazolidinedione may suitably be carried out under analogous conditions to those used in the reaction between a compound of formula (IV) and 2,4-thiazolidinedione.

A compound of formula (VIII) may be prepared from a compound of formula (IV), or a protected form thereof, wherein $R^b$ is $R^a$, by reaction with an appropriate reagent capable of converting $R^a$ to the above defined moiety (b).

Suitable values for $R^a$ include those described above in relation to the compound of formula (II). Appropriate reagents are also described above in relation to formula (II).

Suitable reaction conditions for the reaction of the compound of formula (IV) and the appropriate reagent include those described above in relation to the preparation of compound (II) with the said appropriate reagent.

Suitable protected forms of compounds of formula (IV) are those wherein the aldehyde group is protected. Suitable protecting groups are those used conventionally in the art, although it has been found convenient to protect the aldehyde group by reduction to the hydroxymethyl group, deprotection is conveniently effected by oxidation back to the aldehyde. Suitable reducing agents are conventional agents such as complex metal hydride reducing agents. Suitable oxidising agents are conventional oxidising agents such as $Mn^{IV}O_2$.

In one particular aspect $R^b$ represents a leaving group or atom, especially a fluorine atom.

When $R^b$ represents a leaving group or atom, preferably a fluorine atom, a particularly appropriate reagent is a compound of the above defined formula (V).

The reaction between the compounds of formulae (IV) and (V) may be carried out under any suitable conditions, for example in a solvent such as dimethylformamide or dimethylsulphoxide at an elevated temperature for example in the range of from 60° to 150° C., suitably in the presence of a base such as sodium hydride or potassium carbonate.

The compounds of formula (IV) wherein $R^b$ is a protected form of $R^a$ may be prepared by suitable protection of the corresponding compound of formula (IV) wherein $R^b$ is $R^a$.

The compounds of formula (IV) wherein $R^b$ is hydroxyl or fluorine are known compounds or compounds prepared by methods analogous to those used to prepare known compounds, for example 4-fluorobenzaldehyde and 4-hydroxybenzaldehyde are known commercially available compounds.

The abovementioned conversion of a compound of formula (I) into a further compound of formula (I) includes the reduction of a compound of formula (I) wherein $R^3$ and $R^4$ together represent a bond, to a compound of formula (I) wherein $R^3$ and $R^4$ each represent hydrogen.

The conversion of a compound of formula (I) to a further compound of formula (I) may be carried out by using any appropriate conventional procedure.

A suitable reduction method for the abovementioned reduction includes catalytic reduction or the use of a metal/solvent reducing system.

Suitable catalysts for use in the catalytic reduction are palladium on carbon catalysts, preferably a 10% palladium on charcoal catalyst; the reduction being carried out in a solvent, for example dioxan, suitably at ambient temperature.

Suitable metal/solvent reducing systems include magnesium in methanol.

It will be appreciated that in any of the abovementioned reactions, any reactive group in the compound of formula (I) would be protected, according to conventional chemical practice, where necessary.

Suitable protecting groups in any of the abovementioned reactions are those used conventionally in the art. Thus, for example, a suitable nitrogen protecting group is a benzyl group or a benzyloxycarbonyl group and a suitable hydroxyl protecting group is a benzyl group.

The methods of formation and removal of such protecting groups are those conventional methods appropriate to the molecule being protected. Thus for example an N-benzyl group may be prepared by treatment of the appropriate amine with a benzyl halide, such as benzyl bromide, and thereafter when required the benzyl group may be removed using catalytic hydrogenation.

Where appropriate the isomeric forms of the compounds of formula (I) and the pharmaceutically acceptable salts thereof may be prepared as individual isomers using conventional chemical procedures.

Pharmaceutically acceptable salts and/or solvates of the compounds of formula (I) may be prepared according to conventional procedures.

As mentioned above the compounds of the invention are indicated as having useful therapeutic properties:

The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt thereof and/or a pharmaceutically acceptable solvate thereof for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia, hypertension, cardiovascular disease or certain eating disorders, in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Procedures and Examples illustrate the invention but do not limit it in any way.

Procedure 1

4-(2-Phthalimidoethoxy)benzaldehyde

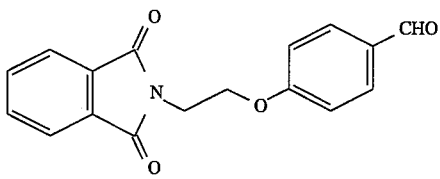

Sodium hydride (60% dispersion in oil, 2 g) was added portionwise to a solution of N-(2-hydroxyethyl)phthalimide (9.6 g) in dry dimethylformamide (70 ml) at room temperature under a nitrogen atmosphere. The mixture was stirred at room temperature for 1 hour prior to the addition of 4-fluorobenzaldehyde (6.2 g, 5.3 ml), and the mixture then heated at 80° C. for 15 hours. The solvent was evaporated and the residue dissolved in water (100 ml) and extracted with ethyl acetate (2×100 ml). The combined ethyl acetate layers were washed with water (2×100 ml), brine (100 ml), dried (MgSO$_4$) and evaporated to yield an oil. The oil was triturated with hexane, and the residue chromatographed on silica gel with 1.5% methanol in dichloromethane to afford the title compound mp 138° C.

$^1$H NMR δ (CDCl$_3$)

4.05 (2H, t); 4.33 (2H, t); 7.10 (2H, d); 7.70–8.10 (6H, complex); and 9.82 (1H, s).

Procedure 2

4-(2-Hydroxyethoxy)benzaldehyde.

A mixture of 4-hydroxybenzaldehyde (45.5 g), sodium hydroxide (15 g) and 2-chloroethanol (30 g, 25 ml) was heated at reflux in water (200 ml) for 7 hours. The mixture was cooled and extracted with dichloromethane (200 ml). The dichloromethane solution was washed with sodium hydroxide solution (2M, 2×150 ml), brine (150 ml), dried (MgSO$_4$) and evaporated to afford the title compound as an oil.

$^1$H NMR δ (CDCl$_3$)

3.15 (1H, br s, exchanges with D$_2$O); 4.15 (4H, complex); 7.07 (2H, d); 7.90 (2H, d); and 9.95 (1H, s).

Procedure 3

5-Benzyl-2,4-thiazolidinedione

Benzaldehyde (10.6 g) and 2,4-thiazolidinedione (11.7 g) were reacted together by a procedure analogous to that described in Example 1. The resulting material, 5-benzylidene-2,4-thiazolidinedione (18.5 g) was dissolved in dioxan (300 ml) and hydrogenated over 10% Palladium-charcoal (18.5 g) at 200 psi, overnight. The mixture was filtered through diatomaceous earth, the filter cake thoroughly washed with dioxan, and the combined dioxan solutions evaporated to afford the title compound, mp 83°–86° C.

$^1$H NMR δ (CDCl$_3$)

3.15 (1H, dd); 3.60 (1H, dd); 4.61 (1H, dd); 7.40 (SH, s); and 9.55 (1H, br s, exchanges with D$_2$O).

Procedure 4

4-[2-(5-Benzyl-2,4,thiazolidinedion-3-yl)ethoxy]-benzaldehyde

Diethyl azodicarboxylate (5.2 g, 4.7 ml) was added dropwise to a stirred, ice-cooled solution of triphenylphosphine (7.9 g), 5-benzyl-2,4-thiazolidinedione (6.2 g) and 4-(2-hydroxyethoxy)-benzaldehyde (5 g) in dry tetrahydrofuran (100 ml). The mixture was allowed to warm to room temperature over 3 hours, and then the solvent was evaporated. The residue was chromatographed on silica gel with hexane-ethyl acetate (2:1 v/v) as solvent to afford the title compound, as a gum.

$^1$H NMR δ (CDCl$_3$)

3.10 (1H, dd); 3.55 (1H, dd); 4.10 (4H, complex); 4.52 (1H, dd); 7.00 (2H, d); 7.30 (5H, s); 7.91 (2H, d); and 10.00 (1H, s).

Procedure 5

4-[2-(5-Phenyl-2,4,thiazolidinedion-3-yl)ethoxy]benzaldehyde

5-Phenyl-2, 4-thiazolidinedione (*J. Amer. Chem. Soc.*, 1967, 89, 647) (0.9 g) and 4-(2-hydroxyethoxy)-benzaldehyde (0.76 g) were reacted together overnight in a procedure similar to that described for Procedure 4. The resulting gum was chromatographed on silica gel with dichloromethane as solvent to afford the title compound as a gum.

$^1$H NMR δ (CDCl$_3$)

4.20 (4H, complex); 5.27 (1H, s); 6.95 (2H, d); 7.30 (5H, s); 7.83 (2H, d); and 9.95 (1H, s).

EXAMPLE 1

5-(4-(2-Phthalamidoethoxy)benzylidene)-2,4-thiazolidinedione

A mixture of 4-(2-phthalimidoethoxy) benzaldehyde (4.3 g), 2,4-thiazolidinedione (1.7 g), benzoic acid (0.5 g) and piperidine (0.5 ml) was heated at reflux in toluene (100 ml) in a Dean and Stark apparatus. After 15 hours at reflux the mixture was allowed to cool and crystallise overnight. The title compound, mp 226°–7° C., was filtered off, washed with cold toluene and dried under vacuum.

¹H NMR δ (DMSO-d₆)

3.92 (2H, distorted t); 4.25 (2H, distorted t) ; 7.00 (2H, d); 7.45 (2H, d); 7.63 (1H, s); 7.80 (4H, s); and 12.00 (1H, br s, exchanges with D₂O).

EXAMPLE 2

5-(4-(2-Phthalimidoethoxy)benzyl)-2,4-thiazolidinedione

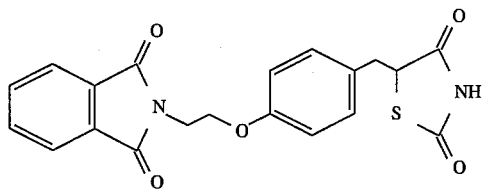

A suspension of 5-(4-(2-phthalimidoethoxy)benzylidene)- 2,4-thiazolidinedione (3.25 g) in dioxan (100 ml) was hydrogenated at room temperature and pressure in the presence of 10% palladium-charcoal (5 g) for 18 hours. A further portion of catalyst (5 g) was added, and the reaction continued for a total of 23 hours. The reaction mixture was filtered through diatomaceous earth, and the solvent evaporated. The resulting gum was crystallised from methanol-dioxan to afford the title compound, mp 192°–4° C.

¹H NMR δ (DMSO-d₆)

3.03 (1H, dd); 3.29 (1H, dd); 3.96 (2H, t); 4.19 (2H, t), 4.84 (1H, dd); 6.84 (2H, d); 7.12 (2H, d); 7.85 (4H, s); and 12.04 (1H, br s, exchanges with D₂O).

EXAMPLE 3

5-(4-[2-(5-Benzyl-2, 4-thiazolidinedion-3-yl)ethoxy]benzylidene)-2,4-thiazolidinedione

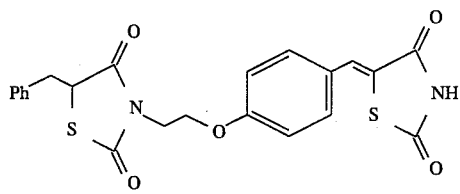

The title compound, mp 145°–7° C., was prepared from 4-[2-(5-benzyl-2,4-thiazolidinedion-3-yl)ethoxy]benzaldehyde (9.1 g) by a procedure analogous to that described in Example 1.

¹H NMR δ (CDCl₃/DMSO-d₆, 1:1)

2.90–3.50 (2H, complex); 3.84 (2H, t); 4.13 (2H, t); 4.95 (1H, dd); 7.10 (2H, d); 7.25 (5H, s); 7.55 (2H, d); 7.77 (1H, s); and 12.25 (1H, br, exchanges with D₂O).

EXAMPLE 4

5-(4-[2-(5-Benzyl-2,4-thiazolidinedion-3-yl)ethoxy]benzyl)-2,4-thiazolidinedione

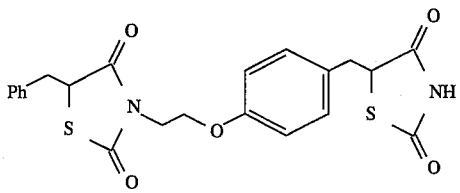

5-(4-[2-(5-Benzyl-2, 4-thiazolidinedion-3-yl ) -ethoxy]benzylidene)- 2,4-thiazolidinedione (3.0 g) was dissolved in dioxan (400ml) and hydrogenated over 10% Palladium-charcoal (6 g) at 150 psi overnight. The reaction mixture was filtered through diatomaceous earth, the filter-cake washed with dioxan, and the combined dioxan solutions evaporated to afford the title compound as a gum. This material was used directly in salt formation.

¹H NMR δ (CDCl₃)

2.90–3.60 (4H, complex) 7 3.95 (4H, complex); 4.40 (2H, complex); 6.77 (2H, d); 7.13 (2H, d); 7.25 (5H, s); and 8.90 (1H, br, exchanges with D₂O).

EXAMPLE 5

5-(4-[2-(5-Benzyl-2,4-thiazolidinedion-3-yl)-ethoxylbenzyl)- 2,4-thiazolidinedione Sodium salt

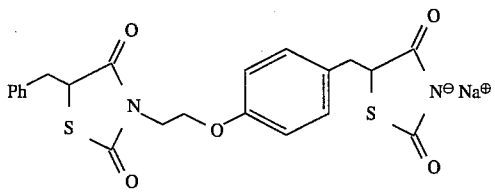

5-(4-[2-(5-Benzyl-2, 4-thiazolidinedion-3-yl)-ethoxy]benzyl)-2,4-thiazolidinedione (2.7 g) was dissolved in ethyl acetate (30 ml) and treated with a solution of sodium 2-ethylhexanoate (0.99 g) in ethyl acetate (20 ml). The title compound, mp 270–274° C., was collected by filtration, washed with ethyl acetate and dried in vacuo over phosphorus (V) oxide.

¹H NMR δ (DMSO-d₆)

2.62 (1H, dd); 3.06 (1H, dd); 3.33 (2H, complex); 3.83 (2H, t); 4.02 (2H, t); 4.07 (1H, dd); 4.96 (1H, dd); 6.76 (2H, d); 7.10 (2H, d); and 7.23 (5H, s).

EXAMPLE 6

5-(4-[2-(5-Phenyl-2,4-thiazolidinedion-3-yl)ethoxy]benzylidene)-2,4-thiazolidinedione

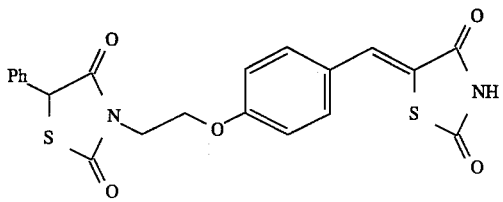

A mixture of 4-[2-(5-phenyl-2,4-thiazolidinedion-3-yl) ethoxy]-benzaldehyde) (1.5 g) 2,4-thiazolidinedione (0.54 g), piperidine (0.4 ml) and benzoic acid (0.2 g) was heated at reflux in toluene (100 ml) in a Dean and Stark apparatus. After 4 hours at reflux the mixture was allowed to cool to room temperature overnight and then evaporated to dryness. The residue was then triturated with diisopropyl ether for 24 hours. The resulting solid was filtered off, washed with ether and dried in vacuo to afford the title compound which softened at 80° C. and melted at 120° C.

$^1$H NMR δ (CDCl$_3$)

4.20 (4H, complex); 5.30 (1H, s); 6.97 (2H, d); 7.30–7.60 (7H, complex); 7.82 (1H, s); and 9.35 (1H, br s, exchanges with D$_2$O).

EXAMPLE 7

5-(4-[2-(5-Phenyl-2,4-thiazolidinedion-3-yl)-ethoxy]benzyl)-2,4-thiazolidinedione

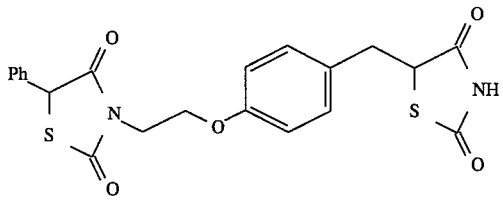

5-4-[2-(5-Phenyl-2,4-thiazolidinedion-3-yl)ethoxy]benzylidene)- 2,4-thiazolidinedione (1.5 g) was hydrogenated at 500 psi in a manner similar to that described for Example 4. After filtration and evaporation of the reaction mixture, the residue was chromatographed on silica gel with ethyl acetate-hexane (1:1 v/v) as solvent to afford the title compound as a foam, mp 67° C.

$^1$H NMR δ (CDCl$_3$)

3.10 (1H, dd); 3.44 (1H, dd); 4.00–4.25 (4H, complex); 4.50 (1H, dd); 5.27 (1H, s); 6.79 (2H, d); 7.13 (2H, d); 7.34 (5H, s); and 8.35 (1H, br s, exchanges with D$_2$O).

DEMONSTRATION OF EFFICACY OF COMPOUNDS

Obese Mice, Oral Glucose Tolerance Test

C57bl/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO: | LEVEL IN DIET (μmol kg$^{-1}$ of DIET) | % REDUCTION IN AREA UNDER BLOOD GLUCOSE CURVE |
| --- | --- | --- |
| 2 | 300 | 42 |
| 5 | 300 | 42 |
| 7 | 300 | 47 |

Toxicology

No toxicological effects were indicated for any of the compounds of the invention in any of the abovementioned tests.

We claim:

1. A compound of formula (I):

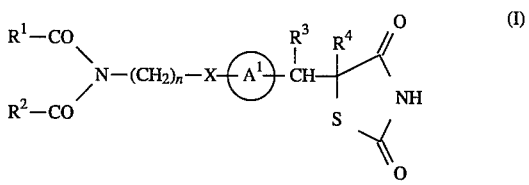

or a tautomeric form thereof and/or a pharmaceutically acceptable salt thereof, and/or a pharmaceutically acceptable solvate thereof, wherein:

R$^1$ and R$^2$ each independently represent an alkyl group, a substituted or unsubstituted aryl group or an aralkyl group being substituted or unsubstituted in the aryl or alkyl moiety;

or R$^1$ together with R$^2$ represents a linking group, the linking group consisting of an optionally substituted methylene group and either a further optionally substituted methylene group or an O or S atom, optional substituents for the said methylene groups being selected from alkyl, aryl or aralkyl or substituents of adjacent methylene groups together with the carbon atoms to which they are attached form a substituted or unsubstituted phenylene group;

R$^3$ and R$^4$ each represent hydrogen, or R$^3$ and R$^4$ together represent a bond;

A$^1$ represents a benzene ring having in total up to three optional substituents;

X represents O or S; and n represents an integer in the range of from 2 to 6.

2. A compound according to claim 1, wherein R$^1$ together with R$^2$ represents a linking group, the linking group consisting of an optionally substituted methylene group and either a further optionally substituted methylene group or an O or S atom, optional substituents for the said methylene groups being selected from alkyl, aryl or aralkyl or substituents of adjacent methylene groups together with the carbon atoms to which they are attached form a substituted or unsubstituted phenylene group.

3. A compound according to claim 2, wherein the linking group consists of an optionally substituted methylene group and an O or S atom, optional substituents for the methylene group being selected from phenyl or benzyl or the linking group consists of two substituted methylene groups wherein the substituents together with the carbon atoms to which they are attached form an unsubstituted phenylene group.

4. A compound according to claim 1, wherein $R^3$ and $R^4$ each represent hydrogen.

5. A compound according to any one of claims 1 to 4, wherein $A^1$ represents a moiety of formula (a):

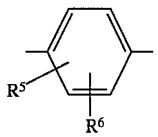

(a)

wherein $R^5$ and $R^6$ each independently represent hydrogen, halogen, substituted or unsubstituted alkyl or alkoxy.

6. A compound according to claim 1, selected from the group consisting of:

5-(4-(2-phthalimidoethoxy)benzylidene) -2,4-thiazolidinedione;

5-(4-(2-phthalimidoethoxy)benzyl)-2,4-thiazolidinedione;

5-(4-[2-(5-benzyl-2,4-thiazolidinedion-3-yl)ethoxy]benzylidene)- 2,4-thiazolidinedione;

5-(4-[2-(5-benzyl-2,4-thiazolidinedion-3-yl)ethoxy]benzyl)- 2,4-thiazolidinedione;

5-(4-[2-(5-phenyl-2,4-thiazolidinedion-3-yl)ethoxy]benzylidene)- 2,4-thiazolidinedione;

5-(4-[2-(5-phenyl-2,4-thiazolidinedion-3-yl)ethoxy]benzyl)- 2,4-thiazolidinedione; or a tautomeric form thereof and/or a pharmaceutically acceptable salt thereof, and/or a pharmaceutically acceptable solvate thereof.

7. A compound according to claim 2 wherein $R^3$ and $R^4$ each represent hydrogen.

8. A compound according to claim 3 wherein $R^3$ and $R^4$ each represent hydrogen.

9. A compound according to claim 2, wherein $A^1$ represents a moiety of formula (a):

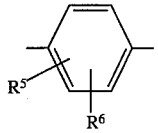

(a)

wherein $R^5$ and $R^6$ each independently represent hydrogen, halogen, substituted or unsubstituted alkyl or alkoxy.

10. A compound according to claim 3, wherein $A^1$ represents a moiety of formula (a):

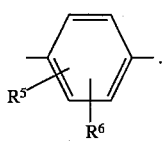

(a)

wherein $R^5$ and $R^6$ each independently represent hydrogen, halogen, substituted or unsubstituted alkyl or alkoxy.

11. A compound according to claim 4, wherein $A^1$ represents a moiety of formula (a):

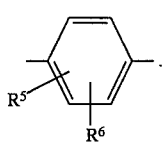

(a)

wherein $R^5$ and $R^6$ each independently represent hydrogen, halogen, substituted or unsubstituted alkyl or alkoxy.

12. A pharmaceutical composition comprising a compound according to claim 1, or a tautomeric form thereof, or a pharmaceutically acceptable salt thereof, or a pharmaceutically acceptable solvate thereof, and a pharmaceutically acceptable carrier therefor.

13. A pharmaceutical composition comprising a compound according to claim 6 and a pharmaceutically acceptable carrier.

14. A method for the treatment and/or prophylaxis of hyperglycaemia, hyperlipidaemia, and hypertension, in a human or non-human mammal which comprises administering an effective, non-toxic, amount of a compound according to claim 1, or a tautomeric form thereof and/or a pharmaceutically acceptable salt thereof and/or a pharmaceutically acceptable solvate thereof to a human or non-human mammal in need thereof.

15. A method for the treatment or prophylaxis of hyperglycemia, hyperlipidemia, and hypertension in a mammal which comprises administering an effective, non-toxic amount of a compound according to claim 6.

* * * * *